United States Patent
Coleman et al.

(10) Patent No.: US 9,700,718 B2
(45) Date of Patent: Jul. 11, 2017

(54) SYSTEMS AND METHODS FOR TREATING HUMAN JOINTS

(71) Applicant: CyMedica, Inc., Scottsdale, AZ (US)

(72) Inventors: Struan Coleman, Locust Valley, NY (US); Jeremy Fryer-Biggs, New York, NY (US); Calvin Domenico, Somerville, MA (US)

(73) Assignee: CYMEDICA, INC., Scottsdale, AZ (US)

( * ) Notice: Subject to any disclaimer, the term of this patent is extended or adjusted under 35 U.S.C. 154(b) by 0 days.

(21) Appl. No.: 14/333,041

(22) Filed: Jul. 16, 2014

(65) Prior Publication Data

US 2014/0330181 A1    Nov. 6, 2014

Related U.S. Application Data

(63) Continuation of application No. 14/021,387, filed on Sep. 9, 2013, now Pat. No. 8,870,798.
(Continued)

(51) Int. Cl.
*A61F 5/00* (2006.01)
*A61N 1/36* (2006.01)
(Continued)

(52) U.S. Cl.
CPC ........ *A61N 1/36003* (2013.01); *A61F 5/0123* (2013.01); *A61F 5/0125* (2013.01);
(Continued)

(58) Field of Classification Search
CPC . A61B 5/02007; A61B 5/7207; A61B 5/7264; A61B 5/022; A61B 5/02028;
(Continued)

(56) References Cited

U.S. PATENT DOCUMENTS

| 4,326,534 A | 4/1982 | Axelgaard et al. |
| 4,765,318 A | 8/1988 | Tranberg et al. |

(Continued)

FOREIGN PATENT DOCUMENTS

| KR | 10-2005-0071489 A | 7/2005 |
| KR | 10-2008-0059551 A | 6/2008 |

(Continued)

OTHER PUBLICATIONS

International Search Report and Written Opinion, which issued in corresponding International Application No. PCT/US14/28698 and mailed Aug. 20, 2014.

(Continued)

*Primary Examiner* — Michael Brown
(74) *Attorney, Agent, or Firm* — Greenberg Traurig LLP

(57) ABSTRACT

A brace includes a closed loop feedback system that provides electrical muscle stimulation (EMS) to a joint of a human patient in response to feedback from the joint and surrounding muscles. In one aspect, a brace for treating a human joint of a patient is provided. The brace includes one or more sensors in physical contact with the skin of the patient and configured to obtain a galvanic reading of resistance of the skin. The brace also includes brace control electronics in communication with the sensor(s) to form a closed loop system via a combination of bracing the joint and electrical muscle stimulation (EMS). The brace control electronics is configured to receive the galvanic reading of the resistance of the skin of the patient and is further configured to instruct the sensor to apply a current/voltage/power onto the skin based on the galvanic reading.

35 Claims, 8 Drawing Sheets

Related U.S. Application Data

(60) Provisional application No. 61/784,927, filed on Mar. 14, 2013.

(51) Int. Cl.
*A61F 5/01* (2006.01)
*A61N 1/04* (2006.01)

(52) U.S. Cl.
CPC ....... *A61N 1/0452* (2013.01); *A61N 1/36014* (2013.01); *A61N 1/0484* (2013.01); *A61N 1/0492* (2013.01)

(58) Field of Classification Search
CPC ....... A61B 5/021; A61B 5/6843; A61B 5/024; A61B 5/681; A61B 5/684; A61B 5/7203; A61B 5/0048; A61B 5/0225; A61B 5/6824; A61B 8/14; A45D 44/22; A61N 5/0613
USPC .......................... 602/16, 20–28; 607/88.101
See application file for complete search history.

(56) References Cited

U.S. PATENT DOCUMENTS

| | | |
|---|---|---|
| 4,796,631 A | 1/1989 | Grigoryev |
| 4,832,033 A | 5/1989 | Maher et al. |
| 5,024,650 A | 6/1991 | Hagiwara et al. |
| 5,052,375 A | 10/1991 | Stark et al. |
| 5,368,546 A | 11/1994 | Stark et al. |
| 5,399,147 A | 3/1995 | Kaiser |
| 5,484,389 A | 1/1996 | Stark et al. |
| 5,507,788 A | 4/1996 | Lieber |
| 5,628,722 A | 5/1997 | Solomonow et al. |
| 5,688,584 A | 11/1997 | Casson et al. |
| 5,766,236 A | 6/1998 | Detty et al. |
| 5,947,913 A | 9/1999 | Palumbo |
| 5,980,435 A | 11/1999 | Joutras et al. |
| 6,321,119 B1 | 11/2001 | Kronberg |
| 6,324,432 B1 | 11/2001 | Rigaux et al. |
| 6,341,237 B1 | 1/2002 | Hurtado |
| 6,350,276 B1 * | 2/2002 | Knowlton ............. A45D 44/22 607/101 |
| 6,456,885 B1 | 9/2002 | Shiba et al. |
| 6,507,757 B1 | 1/2003 | Swain et al. |
| 6,876,883 B2 | 4/2005 | Hurtado |
| 6,944,503 B2 | 9/2005 | Xrowe et al. |
| 6,969,365 B2 | 11/2005 | Scorvo |
| 7,135,005 B2 | 11/2006 | Kania |
| 7,198,610 B2 | 4/2007 | Ingimundarson et al. |
| 7,207,963 B2 | 4/2007 | Kania et al. |
| 7,212,854 B2 | 5/2007 | Kovak et al. |
| 7,341,586 B2 | 3/2008 | Daniel et al. |
| 7,367,935 B2 | 5/2008 | Mechlenburg et al. |
| 7,369,895 B2 | 5/2008 | Hurtado |
| 7,713,225 B2 | 5/2010 | Ingimundarson et al. |
| 7,758,527 B2 | 7/2010 | Gilmour et al. |
| 7,794,418 B2 | 9/2010 | Ingimundarson et al. |
| 7,881,780 B2 | 2/2011 | Flaherty |
| 7,991,461 B2 | 8/2011 | Flaherty et al. |
| 8,016,781 B2 | 9/2011 | Ingimundarson et al. |
| 8,025,632 B2 | 9/2011 | Einarsson |
| 8,070,703 B2 | 12/2011 | Skahan et al. |
| 8,209,030 B2 | 6/2012 | Minogue et al. |
| 8,241,234 B2 | 8/2012 | Ingimundarson et al. |
| 8,257,293 B2 | 9/2012 | Ingimundarson et al. |
| 8,265,763 B2 | 9/2012 | Fahey |
| 8,285,381 B2 | 10/2012 | Fahey |
| 8,311,645 B2 | 11/2012 | Bolea et al. |
| 8,328,746 B2 | 12/2012 | Ingimundarson et al. |
| 8,346,367 B2 | 1/2013 | Carroll |
| 8,355,790 B2 | 1/2013 | Naroditsky et al. |
| 8,433,403 B2 | 4/2013 | Fahey |
| 8,454,543 B2 | 6/2013 | Skahan et al. |
| 8,494,625 B2 | 7/2013 | Hargrove |
| 8,560,077 B2 | 10/2013 | Feinstein |
| 8,588,901 B2 | 11/2013 | Fahey |
| 2002/0068887 A1 | 6/2002 | Kikumoto et al. |
| 2003/0195586 A1 | 10/2003 | Rigaux et al. |
| 2003/0236487 A1 | 12/2003 | Knowlton |
| 2004/0039426 A1 | 2/2004 | Hurtado |
| 2004/0054379 A1 | 3/2004 | Carroll et al. |
| 2004/0059234 A1 * | 3/2004 | Martin ................. A61B 5/022 600/500 |
| 2004/0102723 A1 | 5/2004 | Horst |
| 2004/0210214 A1 * | 10/2004 | Knowlton .............. A61B 18/14 606/41 |
| 2004/0254624 A1 | 12/2004 | Johnson |
| 2005/0131488 A1 | 6/2005 | Hurtado |
| 2005/0215899 A1 | 9/2005 | Trahey et al. |
| 2006/0189899 A1 | 8/2006 | Flaherty et al. |
| 2007/0010772 A1 | 1/2007 | Ryan |
| 2007/0038252 A1 | 2/2007 | Carroll |
| 2007/0129776 A1 * | 6/2007 | Robins ................. A61N 5/0613 607/88 |
| 2007/0179413 A1 | 8/2007 | Imboden et al. |
| 2007/0179414 A1 | 8/2007 | Imboden et al. |
| 2008/0097530 A1 | 4/2008 | Muccio et al. |
| 2008/0228119 A1 | 9/2008 | Ingimundarson et al. |
| 2009/0024062 A1 | 1/2009 | Einarsson |
| 2009/0024065 A1 | 1/2009 | Einarsson |
| 2009/0105558 A1 | 4/2009 | Riley-Doucet et al. |
| 2009/0124948 A1 | 5/2009 | Ingimundarson et al. |
| 2009/0182393 A1 | 7/2009 | Bachinski |
| 2009/0182394 A1 | 7/2009 | Bachinski |
| 2010/0081979 A1 | 4/2010 | Ingimundarson et al. |
| 2010/0082079 A1 | 4/2010 | Skahan et al. |
| 2010/0174221 A1 | 7/2010 | Ingimundarson et al. |
| 2010/0217349 A1 | 8/2010 | Fahey |
| 2010/0262052 A1 | 10/2010 | Lunau et al. |
| 2011/0015696 A1 | 1/2011 | Kirn |
| 2011/0112605 A1 | 5/2011 | Fahey |
| 2011/0184326 A1 | 7/2011 | Ingimundarson et al. |
| 2011/0288611 A1 | 11/2011 | Lunau et al. |
| 2011/0295339 A1 | 12/2011 | Carroll |
| 2012/0136278 A1 | 5/2012 | Gupta |
| 2012/0197343 A1 | 8/2012 | Lane et al. |
| 2012/0289763 A1 | 11/2012 | Boyden et al. |
| 2012/0302821 A1 | 11/2012 | Burnett |
| 2012/0303076 A1 | 11/2012 | Fahey |
| 2013/0030277 A1 | 1/2013 | Fahey |
| 2013/0123568 A1 | 5/2013 | Hamilton et al. |
| 2013/0158456 A1 | 6/2013 | Skahan et al. |
| 2013/0246036 A1 | 9/2013 | Kirn |

FOREIGN PATENT DOCUMENTS

| | | |
|---|---|---|
| KR | 10-1064327 B1 | 9/2011 |
| KR | 10-2012-0028928 A | 3/2012 |
| KR | 10-2013-0091653 A | 8/2013 |
| WO | 2012154633 A1 | 11/2012 |
| WO | 2013-142624 A1 | 9/2013 |

OTHER PUBLICATIONS

Neurotech®—Kneehab XP® Quadriceps Therapy System—On the Move: Clinical News & Insights; Issue 1, Sep. 2010.
Kneehag XP© —Quadriceps Strengthening and Pain Management—Advanced Therapy for Quadriceps Muscle Strengthening and Pain Management <<http://www.neurotechgroup.com/us/products/kneehab-xp>> Retrieved Dec. 17, 2013.

* cited by examiner

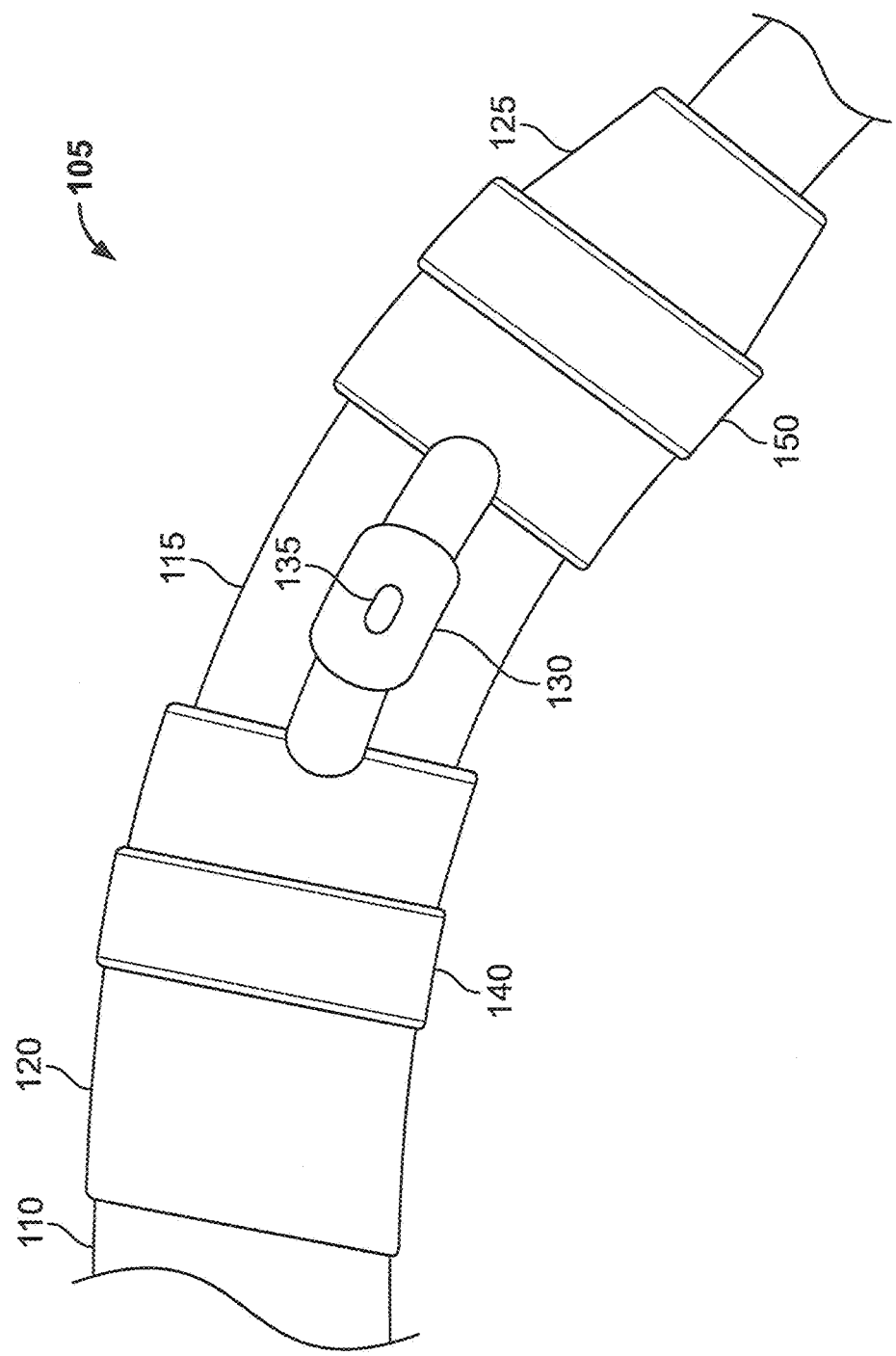

SYSTEMS AND METHODS FOR TREATING HUMAN JOINTS

CROSS REFERENCE TO RELATED APPLICATIONS

This patent application claims the benefit of U.S. patent application Ser. No. 14/021,387, titled "Systems and Methods for Treating Human Joints" filed on Sep. 9, 2013, and Provisional Patent Application Ser. No. 61/784,927, titled "Systems and Methods for Treating Human Joints" filed on Mar. 14, 2013, the contents of which are incorporated herein by reference.

FIELD OF THE INVENTION

The present disclosure relates to systems and methods for treating human joints, and more specifically to systems and methods for treating human joints with a combination of bracing and electrical muscle stimulation in a closed loop system.

BACKGROUND OF THE INVENTION

Orthopedic braces are useful as preventative aids to prevent injuries to joints caused by motions or orientations of the joint that are outside the biomechanical limits of the joint. Orthopedic braces are also useful to promote proper healing of a joint following an injury to, or surgery on, the joint. Braces are also useful as a method to stabilize joints with arthritis, thereby alleviating pain.

Patients usually see a physical therapist to strengthen their muscle(s) after suffering an injury, undergoing surgery, or when afflicted with arthritis, conditions which can result in muscle atrophy. The patient may receive electrical muscle stimulation (EMS) at the start of the physical therapy to loosen their muscles before the exercises and stretching begins. EMS is also used by the therapist (as prescribed by the health care provider) to strengthen muscles which have atrophied. However, the delivery of EMS for muscle strengthening is sub-optimal, as it can only be performed when the patient is with the therapist.

If the patient has been fitted with a brace, the physical therapist may manually adjust the brace, under the guidelines provided by the physician, in order to allow increased motion of the injured joint, or to tighten a brace that has become loose secondary to muscle atrophy, or both. These manual adjustments often lead to errors, as the adjustments are based on the personal judgments of the physical therapist (or medical professional), e.g., the muscles may not be of sufficient strength to support the joint.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs. Significantly, tearing of the ligaments in the knee, particularly the anterior cruciate ligament (ACL), also occur frequently, and in some cases requires surgical intervention for proper healing to occur.

Knee braces in particular are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm or surgically repaired, a knee brace may stabilize, protect, support, or rehabilitate the knee.

Typical knee braces and the prescribing of knee braces have several significant limitations and drawbacks. First, after an injury occurs and a medical professional such as a doctor recommends the patient wear a knee brace, the medical professional may not see the patient again for several weeks to months after the initial visit. The medical professional may not receive any feedback about range of motion of the joint or strength of the muscles surrounding the joint.

Further, a doctor (e.g., surgeon) treating a patient often sees the patient several times after the treatment of the injury (e.g., surgery). The doctor typically determines the next step in the patient's treatment based on how the patient looks and feels during a visit. The doctor, however, usually does not have objective data associated with the patient's injury to help in the doctor's assessment of the patient and the next step in the patient's treatment. Specifically, the doctor may not be able to obtain accurate range of joint motion or muscle strength. As a result, the doctor often determines the patient's next course of treatment based on his or her subjective analysis of the patient at the time of the patient's visit; this analysis may be sub-optimal.

Thus, there remains a need for a brace that is better suited to both stabilize and strengthen an injured joint and, additionally, to provide better objective data about the joint's function in order to facilitate a doctor's treatment of the joint.

SUMMARY OF THE INVENTION

A brace includes a closed loop feedback system that provides both support and electrical muscle stimulation (EMS) to a joint of a human patient in response to feedback from the joint and the surrounding muscles. In one aspect, a brace for treating a human joint of a patient is provided. The brace includes one or more sensors in physical contact with the skin of the patient and configured to obtain a galvanic reading of resistance of the skin. The brace also includes brace control electronics in communication with the sensor(s) to form a closed loop system via a combination of bracing the joint and electrical muscle stimulation (EMS). The brace control electronics is configured to receive the galvanic reading of the resistance of the skin of the patient and is further configured to instruct the sensor to apply a current or voltage onto the skin based on the galvanic reading.

In one embodiment, the galvanic reading of resistance of the skin occurs by measuring the galvanic reading of resistance of a patch of skin between the sensors. In one embodiment, the galvanic reading is across two sensors when the patient's skin forms an electrical circuit between the two sensors. Each sensor does not utilize a gel or a sticky adhesive when in contact with the patient's skin. The sensors may include a first group of sensors in physical contact with a first muscle group and a second group of sensors in physical contact with a second, antagonistic muscle group (or any number of groups on the brace). The first group of sensors stimulates the first muscle group at a first time, and the second group of sensors stimulates the antagonistic muscle group (or any number of groups) at a second time (which may be the same as or different than the first time), resulting in co-coupled contraction.

The brace control electronics may be configured to provide the EMS via a program selected from a plurality of programs. In one embodiment, the brace control electronics receives, via a receiver, a selection of the program (e.g., from the patient, from a medical professional, etc.). In one embodiment, the medical professional can prevent patient control of the brace (e.g., for a period of time).

The brace control electronics can include a pivotal joint configured to enable the brace to flex (e.g., during the patient's flexion and extension). The pivotal joint can include a solenoid and an accelerometer to lock the brace (e.g., after sensing a stress). In one embodiment, the pivotal joint includes a digital positional encoder to determine an absolute position of the joint. The positional encoder may enable adjustment of the physical resistance applied to the joint when the patient moves the joint. The brace control electronics can include a communication module (e.g., transmitter or transceiver or wire) for communicating with the computing device.

In one embodiment, the brace includes an authentication button that, when pressed, indicates that the patient agrees or acquiesces to a program being executed by the brace. The brace can also include visual or tactile feedback, such as during or prior to a set time or event (e.g., an appointment, when the patient is supposed to take medication, etc.).

These and other aspects and embodiments will be apparent to those of ordinary skill in the art by reference to the following detailed description and the accompanying drawings.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1A is a fragmentary perspective view of a knee brace mounted onto the knee of a patient in accordance with an embodiment of the disclosure;

DETAILED DESCRIPTION OF THE INVENTION

Figure 1B:
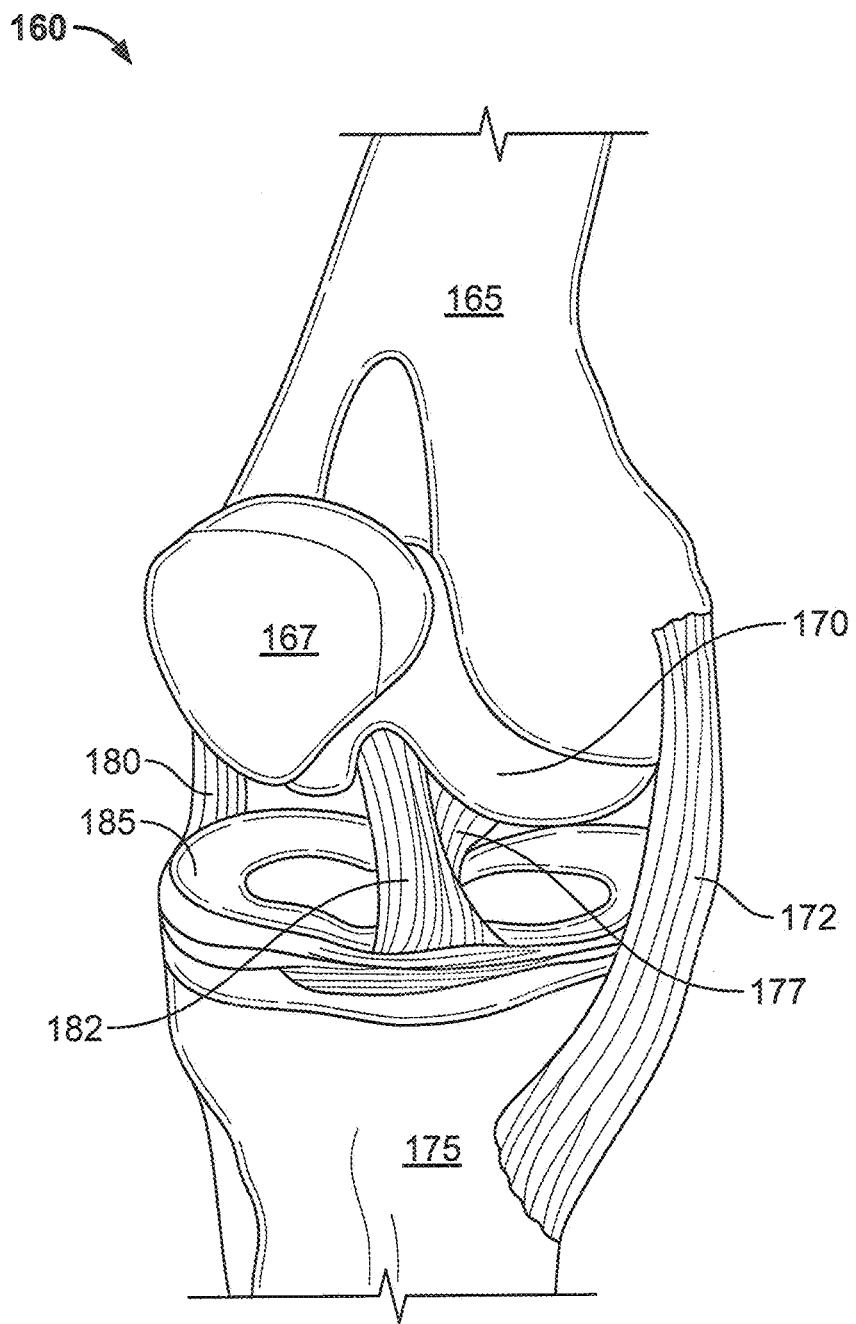
FIG. 1B is a perspective view of a knee joint.

Embodiments are now discussed in more detail referring to the drawings that accompany the present application. In the accompanying drawings, like and/or corresponding elements are referred to by like reference numbers.

Various embodiments are disclosed herein; however, it is to be understood that the disclosed embodiments are merely illustrative of the disclosure that can be embodied in various forms. In addition, each of the examples given in connection with the various embodiments is intended to be illustrative, and not restrictive. Further, the figures are not necessarily to scale, some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Among other things, for example, subject matter may be embodied as methods, devices, components, or systems. Accordingly, embodiments may, for example, take the form of hardware (e.g., electronics hardware and/or physical mechanical hardware), software, firmware or any combination thereof (other than software per se). The following detailed description is, therefore, not intended to be taken in a limiting sense.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, FPGA, or other programmable data processing apparatus, such that the instructions, which execute via the processor of the computer or other programmable data processing apparatus, implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Although described below as a brace associated with a patient's knee, the brace described herein may be used to brace any human joint, such as the hip, shoulder, ankle, elbow, wrist, spine, and/or back. Further, the brace may be used to treat or prescribed/recommended to treat a joint after surgery, for arthritis, after injury, etc.

As described in more detail below, the human knee generally comprises an articulated joint between the thigh and the calf muscles that supports the weight of the human body while the person is standing, walking or running. The knee joint is primarily held together by four ligaments; namely, the anterior cruciate ligament (ACL), the posterior cruciate ligament (PCL), the medial collateral ligament (MCL), and the lateral collateral ligament (LCL). The knee joint can be weakened or damaged by injuries resulting in cartilage damage and ligament strain, which may be the result of trauma, repetitive sporting activities or overly aggressive exercising, or physiological problems such as occurs with the arthritidies. In particular, the human knee may be subjected to a variety of damaging stresses and strains particularly during running and jumping movements. Athletes, in particular, are apt to incur a knee injury as a result of a blow to the knee or to a twisting of the knee, which can commonly occur in various contact sports or high stress sports, such as football, basketball, or skiing.

There are a variety of knee braces available on the market or through healthcare providers. These range from braces that attempt to totally immobilize the knee, to functional braces that may be as simple as flexible elastic bandages that are intended to provide some flexibility while eliminating lateral movement of the ligaments that support the knee. Some of these products are intended to be worn as a relatively permanent device for long-term wear while others are intended to be worn for a short period of time to support a weakened knee during strenuous activities. These functional braces have as their primary object to allow for bending of the knee while preventing any unnatural movement that may aggravate the knee ligaments. Some braces are meant to provide a constant or variable "unloading" force on the knee joint to alleviate pain, such as pain caused by osteoarthritis. While functional braces are intended to allow for a natural movement of the knee joint while a person undergoes walking, running, jumping, skating, etc., they are also intended to prevent sudden movement of the upper and lower legs to one side or the other and to prevent twisting or rotation of the lower leg relative to the upper leg about the vertical axis, and/or to provide a pain-relieving force to the joint.

FIG. 1A is a fragmentary perspective view of a knee brace 105 mounted onto the leg 110 of a person/patient. In one embodiment, the brace 105 is intended to control movement of the thigh to protect the ACL against excessive rotation or extension. In one embodiment, the brace 105 is a closed-loop system that provides electrical muscle stimulation (EMS) based on feedback received from the brace 105 itself. The feedback can be resistance-based feedback, such as feedback based on the amount of resistance that the brace 105 applies to movement of the person's leg 110 or knee 115. As described in more detail below, the feedback may also or alternatively be based on the strength of the knee 115. The feedback may also or alternatively be based on the applied EMS and the knee's response to the EMS. The feedback can be any combination of these types of feedback, such as two or all of the described feedback or any other type of feedback.

The brace 105 includes a proximal end 120 and a distal end 125. The proximal end 120 is typically in physical contact with the person's femur. The distal end 125 is typically in physical contact with the person's tibia. The brace 105 is shown as having an opening at the knee 115. Although shown with an opening, the brace 105 can alternatively be closed at the knee 115.

In one embodiment, the proximal end 120 and distal end 125 of the brace 105 are connected by a pivotal joint or hinge 130. The pivotal joint 130 enables the brace 105 to flex at the joint 130 when the person bends his or her knee 115. As described in more detail below, in one embodiment the pivotal joint 130 includes a digital positional encoder 135 which determines an absolute position of the knee 115. The positional encoder 135 can provide this position of the knee 115 to the brace 105 digitally as part of the feedback in order for the brace 105 to record the position (or, in another embodiment, adjust) based on the transmitted position. In one embodiment, the positional encoder 135 adjusts the resistance applied to the knee 115 when the person moves his or her knee 115 in the brace 105. Although the brace 105 is shown with one pivotal joint 130, the brace 105 can also include a second pivotal joint on the other side of the brace 105 which connects the other side of the proximal end 120 to the other side of the distal end 125. Brace 105 can be made from any of a variety of materials, such as from combinations of metal, foam, plastic, elastic material, composites, and straps.

The brace 105 can be secured to the person's body via one or more connectors 140, 150. In one embodiment, connectors 140, 150 are straps that connect to the brace 105 or to the respective connector 140, 150 itself. Although shown with two connectors 140, 150, any number of connectors may be used. Connectors 140, 150 may be bolts, screws, pins, velcro, strings, clamps, or any other suitable connectors.

FIG. 1B shows a perspective view of the knee joint 160. The femur 165 or thigh bone 165 connects to the patella 167 or kneecap. Articular cartilage 170 lines the bones, cushioning the joint. The medial collateral ligament (MCL) 172 runs down the inside of the knee joint and connects the femur 165 to the tibia 175 (shinbone). The MCL limits the sideways motion of the knee. The posterior cruciate ligament (PCL) 177 also connects femur 165 and tibia 175. The PCL 177 limits backward motion of the tibia 175. The lateral collateral ligament (LCL) 180 runs on the outside of the knee. The LCL limits sideways motion. The anterior cruciate ligament (ACL) 182 connects the femur 165 to the tibia 175 in the center of the knee. The ACL 182 limits rotation and the forward motion of the tibia 175. The meniscus 185 is cartilage that absorbs shock in the joint 160.

Figure 2:
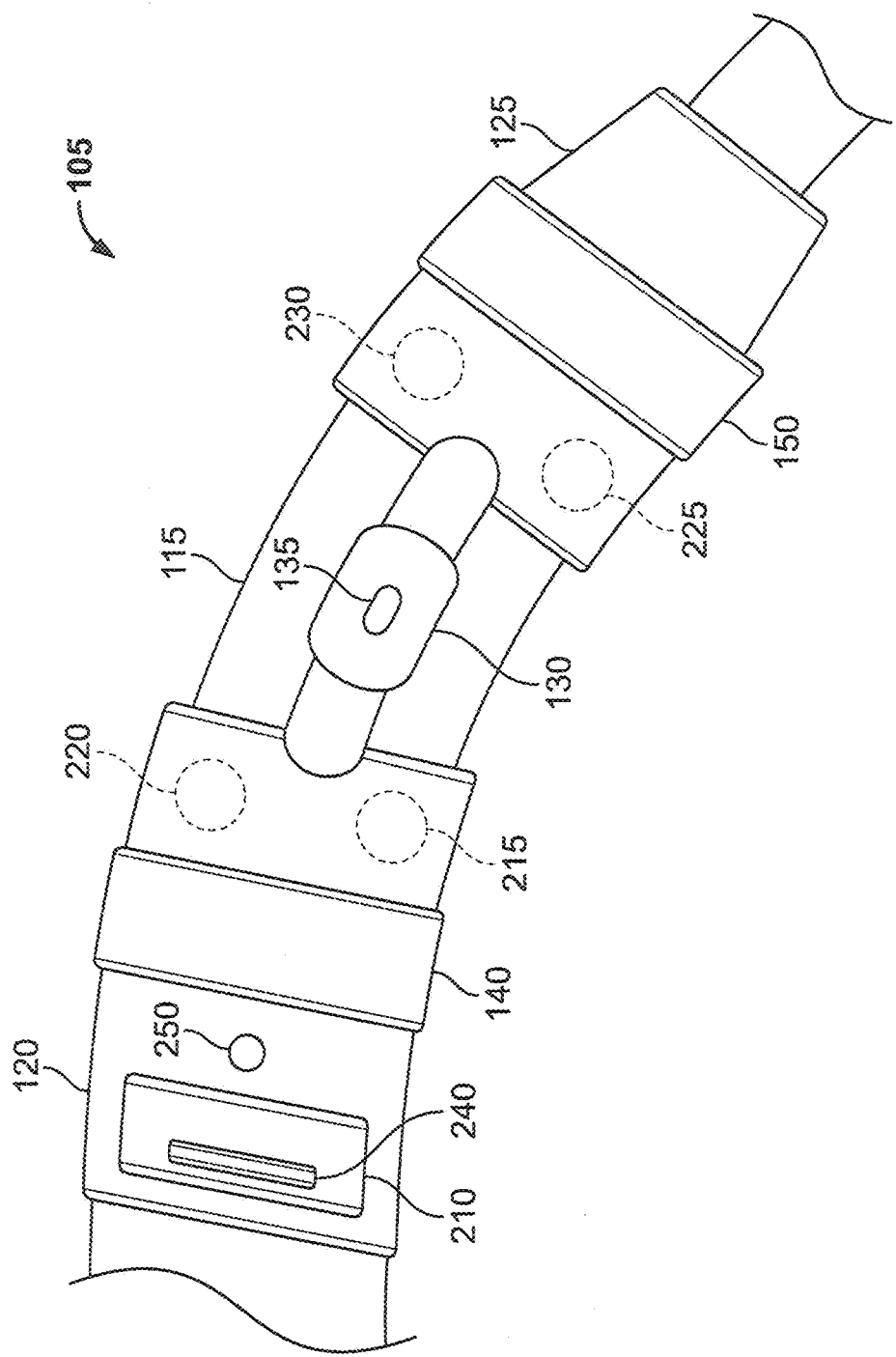
FIG. 2 is a more detailed fragmentary perspective view of a knee brace mounted onto the knee of a patient in accordance with an embodiment of the disclosure.

Also referring to FIG. 2, brace 105 includes brace control electronics 210 attached to or embedded within the brace 105. Although shown as being located in the proximal end 120 of the brace 105, brace control electronics 210 can be embedded within any location of the brace 105, such as within the distal end 125 of the brace 105, within the pivotal joint 130, and/or within one or more of the connectors 140, 150. Further, the brace control electronics 210 can be attached to the brace 105 via one or more cables or wires. In one embodiment, one or more of the components of the brace control electronics 210 is removable from the brace 105.

In one embodiment, the brace control electronics 210 enable EMS of one or more muscles that are in contact with the brace 105. Specifically, the brace 105 includes one or more sensors/pads/electrodes (e.g., sensor 215, 220, 225, 230) positioned in specific locations throughout the brace 105. Although the brace 105 shown in FIG. 2 includes two sensors 215, 220 positioned in the proximal end 120 of the brace 105 and two sensors 225, 230 positioned in the distal end 125 of the brace 105, the sensors 215, 220, 225, 230 can be in any configuration at any location. Further, although brace 105 is shown with four sensors 215, 220, 225, 230, any number of sensors (e.g., six sensors) can be used.

In one embodiment, sensors around the knee are to be positioned as follows: 1) The motor point of the vastus medialis oblique, 2) The motor point of the vastus lateralis, and 3) the motor point of the distal central hamstring. In one embodiment, there are no sensors or electrodes positioned on the calf muscles.

In one embodiment, the sensors 215, 220, 225, 230 are located on the interior wall of the brace 105 so that the sensors 215, 220, 225, 230 come in contact with the person's skin. Each sensor 215, 220, 225, 230 can take a galvanic reading on the person's skin to determine how much the brace control electronics 210 "shocks" the person (i.e., how much current or voltage or power the sensors 215, 220, 225, 230 produce/apply to the person's skin) The majority of the human body's resistance is in the skin—the dead, dry cells of the epidermis (the skin's outer layer) are usually poor conductors. Depending on the person, the resistance of dry skin is usually between 1,000-100,000 Ohms. The skin's resistance is lower if the skin is wet with an electrolytic solution (e.g., from sweat or from moisture). Conventional sensors apply a constant current to a person's skin based on an assumption of 500 Ohms of resistance for the person's skin. Unlike conventional sensors, the sensors 215, 220, 225, 230 of the brace 105 measure the resistance of the skin of the person and adjust the output current/voltage/power based on this measurement. Thus, the quantity of electricity output by one or more of the sensors 215, 220, 225, 230 is based on an electrical reading of the person's skin. In one embodiment, the reading occurs when the person's skin creates a closed circuit across two sensors (e.g., sensors 215, 220 or sensors 225, 230). For example, when a person wears the brace 105, the person's skin on his or her leg closes the circuit between sensor 215 and sensor 220, thereby enabling a galvanic reading to occur. Once this reading is transmitted to the brace control electronics 210, the electronics 210 adjusts the current/voltage/power output produced by the sensors to stimulate the muscles in the person's leg.

In one embodiment, the sensors 215, 220, 225, 230 measure the patient's skin resistance periodically after a predetermined time period has elapsed (e.g., every 5 ms). In another embodiment, a medical professional can instruct the brace control electronics 210 to take a reading at a certain time or for a given amount of time (e.g., measure skin resistance every 5 ms from 6 PM to 7 PM). The medical professional or the brace 105 itself can also be programmed to "shock" the patient at a predetermined time or times or on a specific schedule.

Further, conventional sensors or pads typically require the use of an electrolytic gel to facilitate conduction of the current/voltage/power output by the pads. The use of an electrolytic gel is problematic because it is messy and causes the surrounding material (e.g., on a brace) to slide or move as the patient moves. Further, gel would not be useable in the brace 105 because gel creates a virtual short circuit at the location of contact with the sensor 215, 220, 225, 230. Thus, the sensor 215, 220, 225, 230 would not be able to measure the resistance of the skin if gel were used. Unlike conventional sensors, the sensors 215, 220, 225, 230 are not used with gel. Instead, the sensors 215, 220, 225, 230 are conductive silicon material that creates an electrical connection with a person's skin (e.g., via sweat, moisture, or skin itself). In one embodiment, the sensors 215, 220, 225, 230 are silicon with metal impregnated into the silicon, such as silicon nickel. Other conductive materials may be used, such as aluminum and/or carbon nanoparticles.

Additionally, many conventional pads stick to the patient's skin in order to make adequate contact with the skin. This causes problems, such as that the stickiness of the pad will cause hair or skin to be removed when the pad is removed or moved (e.g., as the brace moves or bends). Unlike these conventional sensors, sensors 215, 220, 225, 230 do not use any sticky substance to connect to the patient's skin. Instead, the sensors 215, 220, 225, 230 make physical contact with the skin via the placement of the sensors 215, 220, 225, 230 in the brace 105.

The brace control electronics 210 receives feedback from one or more of the sensors 215, 220, 225, 230 and/or the positional encoder 135, thereby forming a closed loop system. Specifically, the brace 105 delivers EMS to the muscle via one or more of the sensors 215, 220, 225, 230 and adjusts the amount of current/voltage/power delivered by one or more of the sensors 215, 220, 225, 230 based on the readings obtained by the sensors 215, 220, 225, 230 and communicated to the brace control electronics 210.

In one embodiment, the brace control electronics 210 includes a microprocessor (e.g., ARM® CORTEX™ microprocessor developed by ARM® Ltd. of San Jose. Calif.) with one or more batteries and a communications module such as a Bluetooth® transceiver/module. The brace control electronics 210 can provide stimulation via the sensors 215, 220, 225, 230 via any type of waveform or signal, such as a parabolic arc (e.g., start soft and progressively increase resistance), sine wave, cosine wave, pulse width modulation (PWM), pulse density modulation (PDM), square wave, sawtooth wave, etc. Further, the brace control electronics 210 can provide waveforms with any pulse duration and any pulse width. Bluetooth® registered trademark of Bluetooth® SIG Inc.

Additionally, the brace control electronics 210 includes one or more digital-to-analog converters (DACs) (e.g., 24-bit DACs) that bias a transistor located in front of the battery. In one embodiment, leakage occurs through the transistor via the battery. There are also operational amplifiers (op-amps), transformers, inductors, and/or switch mode regulators to step up a few volts to, e.g., 80-110 V DC and I<=40 mA. In one embodiment, the DACs and op-amps, transformers, inductors, and/or switch mode regulators are controlled via software.

In a further embodiment, the brace control electronics 210 adjusts the current/voltage/power delivered to the sensors 215, 220, 225, 230 based on feedback from the positional encoder 135 and/or the sensors 215, 220, 225, 230. In one embodiment, one or more of the sensors 215, 220, 225, 230 behave differently depending on the position of the knee. Additionally, every person's skin resistance is different, and the brace control electronics 210 can measure the skin resistance of the patient via the sensors 215, 220, 225, 230 and adjust the output current/voltage/power based on this reading or readings. Thus, in one embodiment, a medical professional may set the brace to level 3 stimulation for person A because person A has sensitive skin, and may set the brace to level 6 stimulation for person B because person B has "thick" skin and is not as sensitive to the stimulation. In another embodiment, the level stimulation is set automatically based on the feedback. In yet another embodiment, the patient sets the level stimulation via a knob or control on the brace 105.

The brace control electronics 210 may also adjust the amount of support/stabilization provided by the brace 105 based on feedback from the positional encoder 135. For example, the brace 105 may lock, unlock, or limit the range of motion (i.e., angle of movement) of the brace 105 (e.g., how far the brace 105 bends) depending on how much the knee 115 needs to be stabilized. If the knee 115 is unstable, such as immediately after surgery was performed to repair the person's ACL, the brace 105 may not brace as much. If the person is sitting down and gets up from a chair, the brace 105 (i.e., the brace control electronics 210) may sense this action via feedback from the positional encoder 135 and may brace or stabilize the knee 115 more.

If the brace control electronics 210 senses a stress, the pivotal joint 130 may lock. In one embodiment, the brace control electronics 210 includes an accelerometer (e.g., a data gathering accelerometer) with a solenoid to perform the locking of the brace 105. For example, if the person stumbles or takes a quick step, the brace 105 may restrict the person's movement to protect the knee 115. The brace 105 may also protect the knee 115 more (or less) significantly based on the time period, such as by limiting the knee's movement during the first three months after surgery.

As described in more detail below, the brace 105 may communicate data generated by the brace control electronics 210 and/or the feedback provided by the sensors 215, 220, 225, 230 and/or the positional encoder 135 to a medical professional (e.g., doctor, surgeon, and/or physical therapist). The medical professional may adjust the brace 105 based on this data. For example, the brace 105 may measure how strong the muscles surrounding the knee 115 are getting based on the EMS and/or the range of motion of the knee 115 (obtained via the positional encoder 135). As described in more detail below, the medical professional can utilize this feedback and data to adjust the treatment of the patient. For example, the medical professional may adjust the brace 105 based on these readings. Thus, brace 105 provides a combination of bracing a joint and simultaneously stimulating the muscle(s) around the joint.

Additionally, athletes or coaches may be interested in statistics produced by the brace control electronics 210, such as determining how much an athlete's joint can move after an injury or during recovery. As a specific example, a pitching coach on a baseball team is likely interested in statistics associated with a pitcher's movement of his pitching arm.

In one embodiment, the brace control electronics 210 includes one or more brace control programs that a medical professional or patient can select and/or program. The brace control programs may be dynamic (e.g., changeable or variable, not a fixed frequency, not fixed timing, not a fixed waveform, etc.) and may cause different types of EMS to be executed on different parts of the patient's body. For example, if the feedback data from the brace control electronics 210 indicates that the patient's vastus medialis oblique muscles are getting stronger while the patient's distal central hamstring (or, in another embodiment, the patient's calf muscle) is not getting stronger, a medical professional (e.g., doctor or physical therapist) may instruct, via one or more of these programs, the brace 105 to execute a predetermined brace control program. This predetermined brace control program may cause sensors 215, 220 to output a current of 7 mA of DC current for 30 seconds and then 5 mA for 20 seconds. The predetermined brace control program may further cause sensors 225, 230 to output a current of 1 mA for 50 seconds, thereby providing significantly more stimulation to the patient's vastus medialis oblique muscles compared with the patient's distal central hamstring (or, in another embodiment, the patient's calf muscle). In one embodiment, the brace 105 includes specific programs for the first week after surgery, specific programs for the first month after surgery, specific programs for arthritis, etc.

In one embodiment, the brace 105 includes an authentication button 250. The authentication button 250 is a button that has to be pressed by the patient in order for a program to execute. Thus, the authentication button 250 is a security feature of the brace 105—the brace 105 cannot be compromised or caused to execute one or more stimulation programs or actions until the wearer of the brace presses the authentication button 250. For example, if a medical professional remotely accesses the brace control electronics 210 and attempts to have the brace 105 execute specific muscle stimulation or adjust the range of motion of the brace 105 for the patient, the brace 105 will not execute the stimulation or adjust the range of motion until the patient presses the authentication button 250.

The brace control electronics 210 may also include a display 240. The display 240 may display statistics associated with the brace, such as how much resistance the sensors 215, 220, 225, 230 are measuring, how much current/voltage/power the sensors 215, 220, 225, 230 are delivering, how much force the positional encoder 135 is delivering, the angle of the positional encoder 135, programs executing or past programs executed, the date, the time, the patient's next appointment (e.g., with a doctor or a physical therapist), average range of motion of the joint over a fixed period of time or any other information associated with the brace 105. In one embodiment, the brace control electronics 210 includes a keyboard to enable the user to provide input to brace 105.

The brace 105 may also provide tactile feedback. For example, the brace 105 may include a motor that causes a portion of or all of the brace 105 to vibrate. This tactile feedback may occur based on settings provided to the brace 105 by the patient or by a remote user (e.g., a medical professional). For instance, the brace 105 may provide tactile feedback when the patient has not moved his limb for a predetermined amount of time, when the joint has flexed further than or close to a maximum angle, as a warning (e.g., a warning set by the patient), as a reminder (e.g., a reminder that the patient has a medical appointment in 15 minutes), etc.

The brace 105 may also have visual feedback. For example, one or more LEDs can be located on the brace 105 for alerting the patient of a specific occurrence. For instance, an LED can light when the brace 105 is waiting for the patient to press the authentication button 250.

Additionally, the brace 105 may transmit the generated data (feedback data) to a computing device associated with, for example, the user or the medical professional. Due to the communication of the brace 105 with the computing device, the medical professional can be notified or will see that the patient is not wearing the brace if the measured resistance is infinite. Similarly, if the patient falls into a pool, the medical professional will know this as well because the measured resistance will be a short (e.g., approx. zero ohms).

In one embodiment, the medical professional or brace 105 can transmit the data generated by the brace 105 to an insurance company. The insurance company can then determine, from this data, whether the patient is performing his or her exercises, is wearing the brace throughout the day, etc. This may affect the insurance provided by the insurance company (e.g., lower premium if patient wearing brace all day and doing exercises).

In one embodiment, the brace 105 is an unloader brace. Unloader braces are usually prescribed for people who have medial (inner part of the knee) compartment knee osteoarthritis. These knee braces unload stress from the affected joint by placing pressure on the thigh bone. This forces the knee to bend away from the painful area. Thus, an unloader brace is a brace that is stronger and more rigid on one part of the knee. In one embodiment, brace 105 exerts a force on one direction of the knee. In one embodiment, an adapter piece attaches to the brace 105 to exert such a force, thereby forming an unloader brace.

The brace 105 may also be configured to provide co-coupled contraction of different muscle groups. For example, four sensors (e.g., including sensors 215 and 220) can be located on the quadriceps muscles and two sensors (e.g., sensors 225 and 230) can be located on the hamstring muscles. The brace 105 can stimulate both sets of muscles at different times or simultaneously, such as at the same or at different frequencies, patterns, and/or waveforms. For example, when the brace 105 activates or fires the sensors 215, 220 at a first rate, the brace 105 can activate or fire the sensors 225, 230 at a second, slower rate (or, in another embodiment, at the same rate). The firing of the hamstring at a different frequency than (or at the same time as) the quadriceps muscles results in co-coupled contraction. The firing of the hamstring (the antagonistic muscle group) with the quadriceps muscles results in the strengthening of both sets of muscles. The stimulation of the antagonistic muscle group strengthens both sets of muscles, even when only one of the muscle groups is atrophied. In one embodiment, the brace 105 can be programmed to execute a first program for a first muscle and execute a second program for a second, antagonistic muscle. In one embodiment, the doctor positions the sensors 215, 220, 225, 230 on the brace 105 for this co-coupled contraction to occur. In another embodiment, the sensors 215, 220, 225, 230 are integrally positioned within the brace 105 to cause the co-coupled contraction of different muscle groups.

In one embodiment, the brace 105 monitors muscles passively. In other words, the sensors 215, 220, 225, 230 take galvanic readings when firing and/or when not firing. The readings obtained when the sensors 215, 220, 225, 230 are not firing result in data to determine how strong the muscle has gotten due to treatment from the brace 105.

In one embodiment, the brace 105 includes a data gathering thermometer which can determine the temperature of the patient and adjust one or more of the sensors 215, 220, 225, 230 and/or the brace control electronics 210 based on this temperature.

Figure 3:
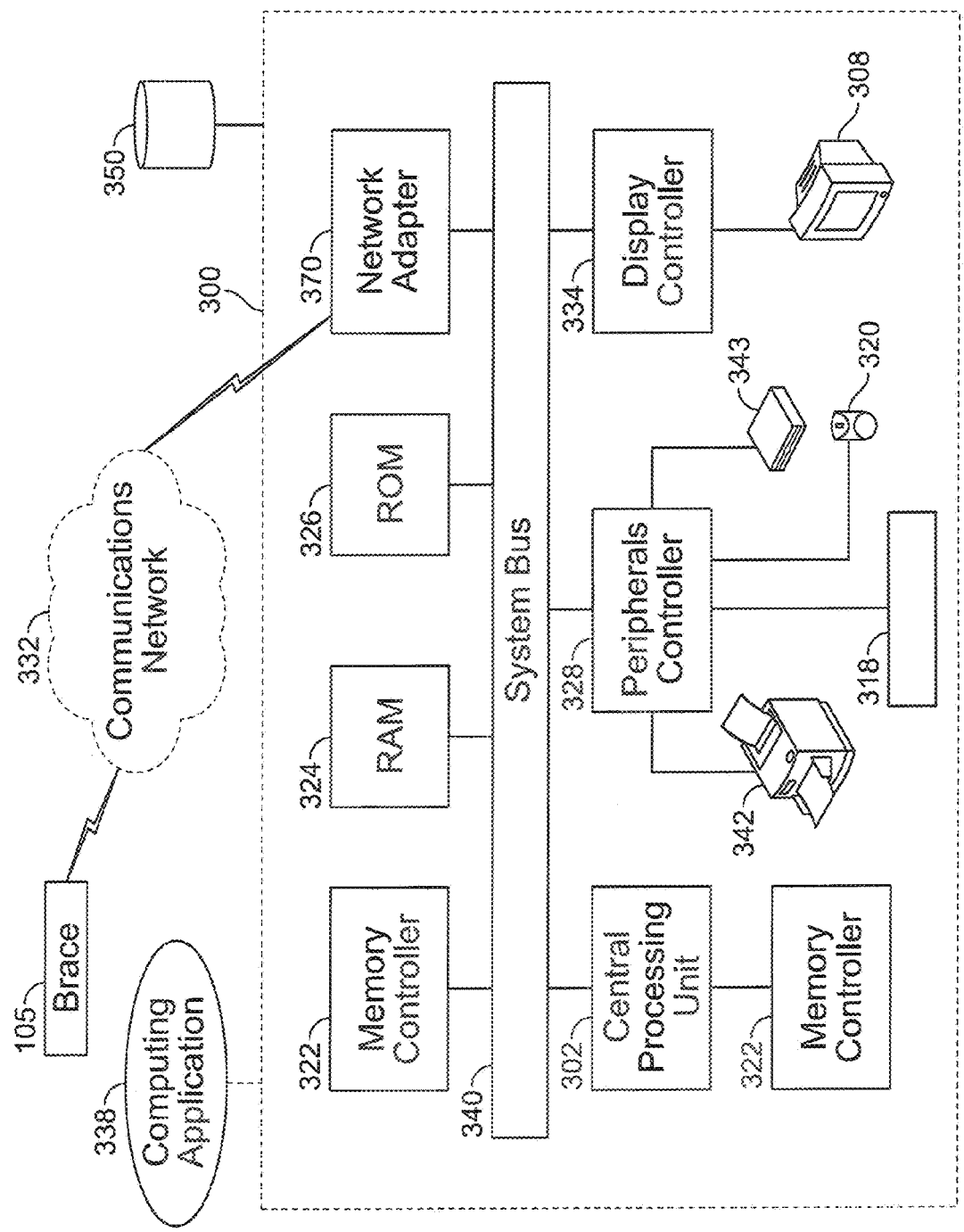
FIG. 3 is a block diagram of the knee brace of FIG. 1 in communication with a computing device in accordance with an embodiment of the disclosure.

Referring to FIG. 3, the brace 105 (brace control electronics 210) can be configured to communicate (e.g., wirelessly or via a wired connection) with a computing device 300. Examples of the computing device 300 include, but are not limited to, personal computers, digital assistants, personal digital assistants, mobile phones, smartphones, tablets, or laptop computers. The computing device 300 may be the patient's device or a device associated with a medical professional. This can enable the medical professional to retrieve and analyze data transmitted from the brace 105. In one embodiment, this data is transmitted in real-time, so that the medical professional can analyze the data and/or adjust the brace 105 at any time.

Computer device 300 is a logic apparatus adapted and configured to read instructions from media and/or a network port. Computing device 300 can be connected to the Internet or an intranet. The device 300 includes a central processing unit (CPU) 302, one or more memory (e.g., RAM 324 and/or ROM 326), optional input devices, illustrated as keyboard 318 and/or mouse 320 and optional monitor 308. In one embodiment, the computing device 300 is in communication with or is a server computer. The computing device 300 can include any suitable means of transmitting and/or receiving data. For example, the computing device 300 can have a network connection, a wireless connection or an internet connection. It is envisioned that data relating to the present disclosure can be transmitted over such networks or connections.

The computing device 300 is capable of, or in at least some situations adaptable for, executing a variety of computing applications 338, including computing applications, a computing applet, a computing program, or other instructions for operating on computing device 300 to perform at least one function, operation, and/or procedure. Computing device 300 is controllable by computer readable storage media for tangibly storing computer readable instructions, which may be in the form of software. The computer readable storage media capable of, or in at least some situations adaptable to, tangibly store computer readable instructions can contain instructions for computing device 300 for storing and accessing the computer readable storage media to read the instructions stored thereon themselves. Such software may be executed within CPU 302 to cause the computing system 300 to perform desired functions.

As will be appreciated by those skilled in the art, a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

In operation, the CPU 302 fetches, decodes, and executes instructions, and transfers information to and from other resources via the computer's main data-transfer path, system bus 340. Such a system bus connects the components in the computing device 300 and defines the medium for data exchange. Access to the RAM 324 and/or ROM 326 may be controlled by memory controller 322. The memory controller 322 may provide an address translation function that translates virtual addresses into physical addresses as instructions are executed.

In addition, the computing device 300 can contain peripherals controller 328 responsible for communicating instructions from the CPU 302 to peripherals, such as, printer 342, keyboard 318, mouse 320, and data storage drive 343. Display 308, which is controlled by a display controller 334, is used to display visual output generated by the computing device 300. Such visual output may include text, graphics, animated graphics, and video. The display controller 334 includes electronic components required to generate a video signal that is sent to display 308. Further, the computing device 300 can contain network adaptor 336 which may be used to connect the computing device 300 to an external communications network 332.

By way of example, Bluetooth® products may be used to provide links between brace 105 and mobile computers, mobile phones, portable handheld devices, personal digital assistants (PDAs), tablets, and other mobile devices and connectivity to the Internet. Bluetooth® is a computing and telecommunications industry specification that details how mobile devices can easily interconnect with each other and with non-mobile devices using a short-range wireless connection.

The computing device 300 may utilize a specific application 338 (also referred to as an "app") to communicate with and/or program the brace 105. In one embodiment, the computing device 300 downloads the app 338 from the communications network 332 (e.g., from an "app store" on the Internet). The app 338 may provide statistics, graphs, normalized data, raw data, averages (e.g., average flexion and average extension), real-time data, etc. to the medical professional. In one embodiment, the app 338 provides output data that is in a format customized by the user or medical professional. In one embodiment, the app 338 communicates with other programs, such as hospital software, word processing software (e.g., Microsoft Word®), spreadsheet software (e.g., Microsoft Excel®), email software (e.g., Microsoft Outlook®), publishing software (e.g., Microsoft Powerpoint®), etc. (e.g., to further analyze or display the data). The app 338 may provide a graphical user interface (GUI) or a text-based user interface. The app 338 communicates with the brace 105 and/or a database (as described below) to display and analyze the data generated by the brace 105 (and/or doctor). In one embodiment, the app 338 can program the brace 105, such as by the patient or the doctor. In one embodiment, and as described above, the patient has to press the authentication button 250 in order for the brace 105 to actually execute the program being set remotely.

In yet another embodiment, the computing device 300 is a portable data reader that is specifically associated with the brace 105. For example, a medical professional can synchronize the reader 300 with the patient's brace 105 when the medical professional provides the brace 105 to the patient. At some later time (e.g., at a subsequent visit), the medical professional can use the reader to capture data from the brace 105. The medical professional can then use the reader to view the retrieved data (during the patient's visit and/or before the visit).

In at least some configurations, a user executes a browser to view digital content items and can connect to a server via a network, which is typically the Internet, but can also be any network, including but not limited to any combination of a LAN, a MAN, a WAN, a mobile, wired or wireless network, a private network, or a virtual private network.

In one embodiment, the computing device 300 is in communication with a database 350. The computing device 300 may store data transmitted by the brace 105 in database 350. The database 350 may be an internal database of the computing device 300. Alternatively, the database 350 may be an external database in communication with the computing device 300.

To protect patient confidentiality and to protect the security of the data, usage data that is transmitted from the devices (via Bluetooth®, WiFi, or via other means) is encrypted to ensure that only the patient or the patient's doctor can obtain access to this medical information. The encryption can be done via either software executing on the processor or via external hardware that processes the data before it is transmitted. In one embodiment, each set of logs is uniquely tied to the device that created them. This can be done by the device tagging the data being transmitted from the device with a unique identifier associated with the device itself. The unique identifier is set either by the processor or by an external component of the system (e.g., UUID chip).

The database 350 can be used by, for example, doctors or medical professionals to retrieve, review, and/or analyze the data from the brace 105. The doctors may utilize the data from the brace in the doctor's analysis or recommendations to the patient. Further, doctors may utilize the data from the brace 105 of one patient in recommendations to other patients with similar conditions or injuries. For example, if the doctor tells a patient recovering from an ACL reconstructive surgery to execute program 1 for the first week and to execute program 2 for the second week, and if the doctor sees significant improvements in the patient's strength in the patient's knee due to these programs, the doctor will likely tell another patient recovering from a similar surgery to execute the same programs during the same time periods. The doctor can then obtain data from both patients to see how they are responding to the brace 105 and the programs being executed by the brace 105.

In one embodiment, the brace 105 includes a distress or panic button. When pressed, the distress/panic button may notify a medical professional (e.g., doctor) or service that the patient needs assistance (e.g., has fallen and has hurt himself). The medical professional or service can then travel to the patient's location to assist the patient or call the patient to determine what is wrong. In one embodiment, the pressing of the panic/distress button results in a flag being set at the given time in the data. The flag may indicate what the patient was doing during that time, such as what absolute position the pivotal joint 130 was in (and therefore the position that the knee was in), what EMS was being executed, etc. This flag may also indicate to the medical professional that the patient did not take his or her medication at a previously designated time.

Figure 4:
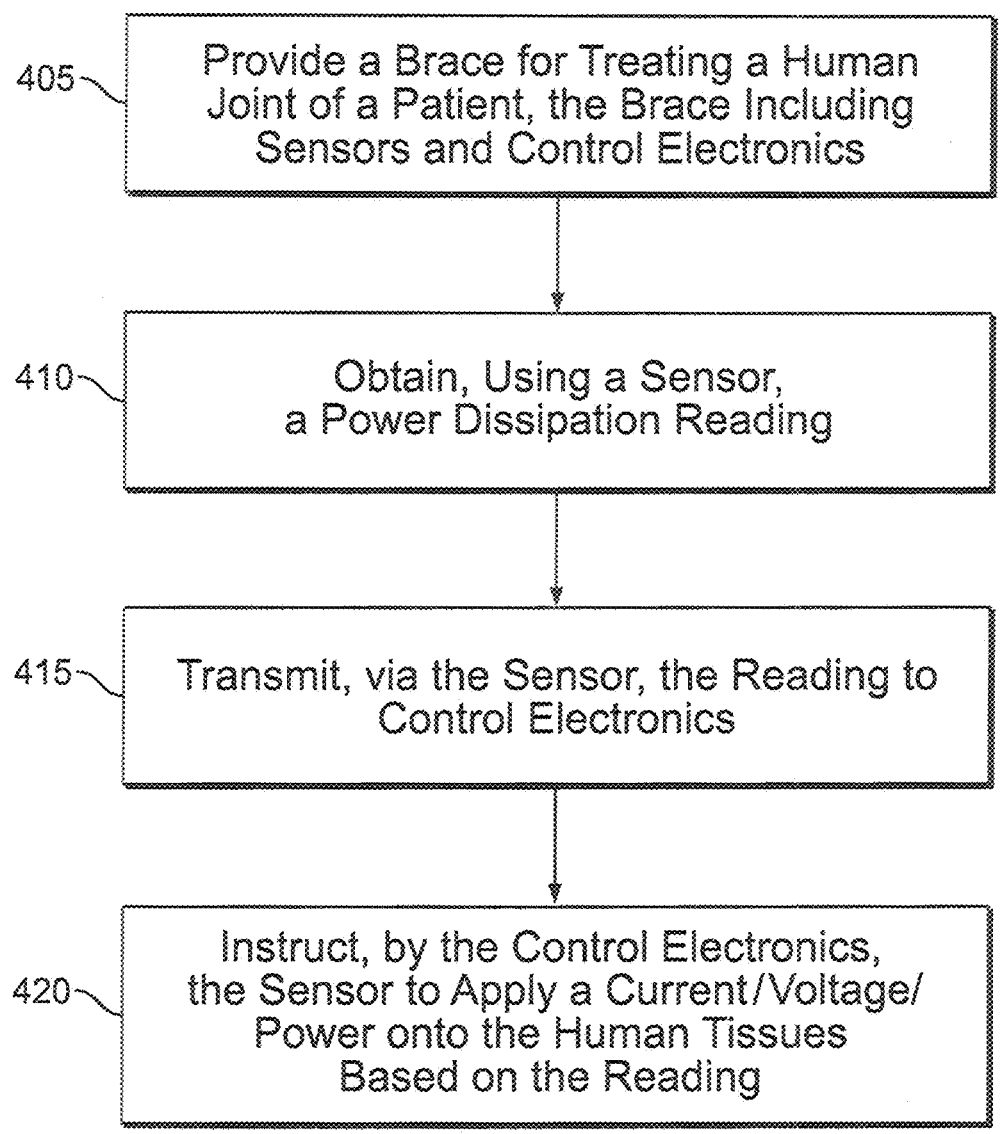
FIG. 4 is a flow diagram of an example of steps performed according to the disclosure.

FIG. 4 shows a flowchart illustrating an embodiment of steps performed in the closed loop feedback bracing system. A brace is provided for treating a human joint of a patient (e.g., knee, elbow, back, spine, wrist, etc.) (Step 405). The brace includes sensors and brace control electronics. One or more sensors 215, 220, 225, 230 obtain a galvanic reading of resistance of the skin (Step 410). As described above, in one embodiment two sensors obtain a resistance reading when skin completes the circuit between the two sensors. The sensor or sensors 215, 220, 225, 230 then transmit the resistance reading to the brace control electronics 210 (Step 415). The brace control electronics 210 instruct the sensor or sensors 215, 220, 225, 230 to apply a current/voltage/power onto the skin based on the galvanic reading (Step 420). This results in a closed loop feedback system, where the output of the brace 105 is dependent upon the input readings of resistance (e.g., of sweat, of skin, etc.). In one embodiment, the output of the brace 105 is dependent upon both the input readings of resistance from the sensors 215, 220, 225, 230 and the physical resistance of the positional encoder 135 as described above.

Figure 5:
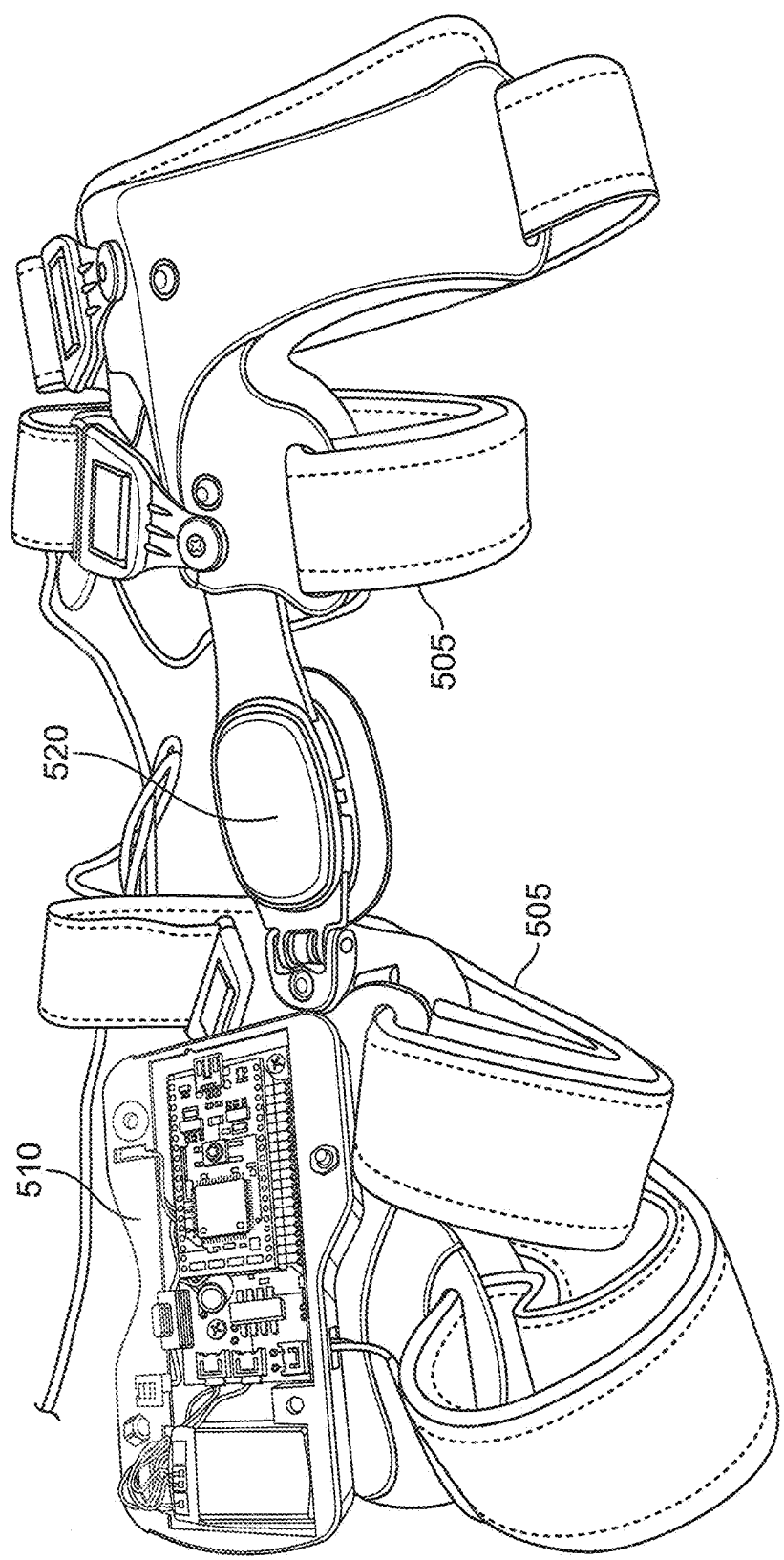
FIG. 5 is a perspective view of a knee brace according to the disclosure.
Figure 6:
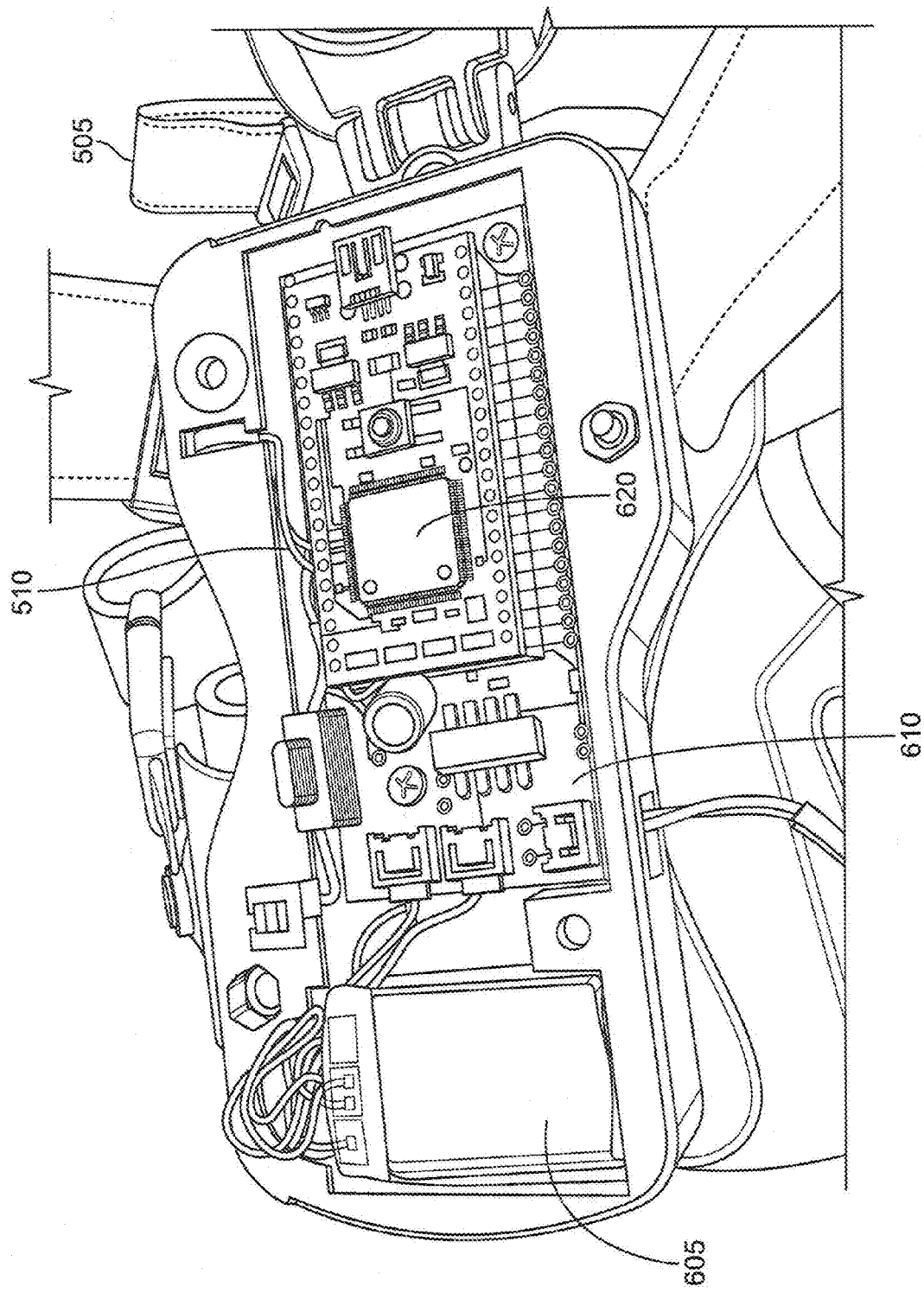
FIG. 6 is a perspective view of brace control electronics of a knee brace according to the disclosure.
Figure 7:
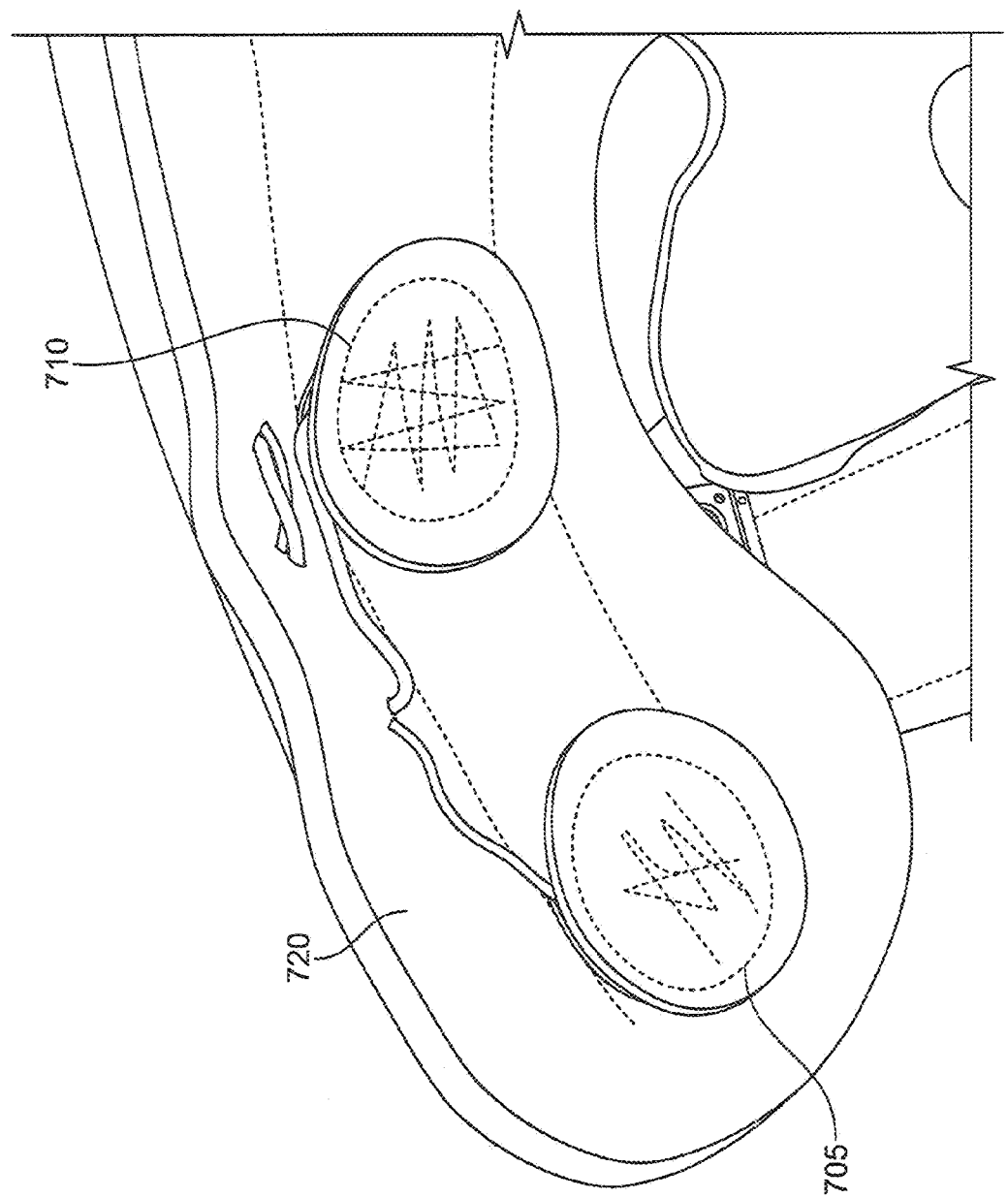
FIG. 7 is a perspective view of sensors of the knee brace according to the disclosure.

FIG. 5 is a perspective view of an embodiment of a knee brace 505 including brace control electronics 510 and a pivotal joint 520. FIG. 6 is a more detailed perspective view of brace control electronics 510 of the knee brace 505. The brace control electronics 510 include a battery 605 connected to a circuit board 610. The circuit board 610 includes a microprocessor 620 for the programming of and functioning of the brace 505. FIG. 7 is a perspective view of two sensors 705, 710 of the knee brace 720. The sensors 705, 710 are located on the interior wall of the brace 720 so that the skin of the wearer of the brace is in physical contact with the sensors 705, 710.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the user computing device or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

While the system and method have been described in terms of one or more embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A system comprising:
at least one sensor comprising a plurality of electrodes including at least one active electrode and at least one receiving electrode, the at least one sensor configured and arranged to be in physical contact with skin of a patient forming an electrical circuit with control electronics of a control means, the electrical circuit configured and arranged to measure a resistance of the skin using the at least one active electrode and at least one receiving electrode, and to form a closed loop electrical muscle stimulation system, wherein a stimulation current or voltage applied by the sensor onto the skin between the at least one active electrode and at least one receiving electrode is based on at least one program stored on a first computer readable medium and the resistance of the skin measured through the at least one active electrode and at least one receiving electrode,
the control means for (a) applying a sense electrical pulse to the tissue using the at least one sensor, (b) measuring at least one electrical parameter from the tissue related to power dissipation of the sense electrical pulse in the tissue, (c) using at least one of the active electrodes, adjustably apply a stimulation pulse to the tissue based at least in part on the measured power dissipation, the stimulation being adjustably controlled by the control means to maintain a constant power output to the tissue based at least in part on the at least one electrical parameter, and (d) repeat steps (a)-(c);
a brace configured to store usage data on at least one of the first computer readable medium and a second computer readable medium, the usage data relating to the patient's use of the brace; and
a computing program, applet or application configured to upload usage data for analysis.

2. The system of claim 1, wherein the computing program, applet or application is configured for use by a medical professional to monitor patient compliance with instructions provided by the medical professional.

3. The system of claim 1, wherein the computing program, applet or application is configured for use by an insurance company to determine patient compliance with instructions provided by a medical professional.

4. The system of claim 1, further including a positional encoder configured to provide range of motion data.

5. The system of claim 1, further including an accelerometer configured to provide acceleration data related to use of the brace.

6. The system of claim 1, wherein the computing program, applet or application is configured to enable a medical professional to analyze range of motion data over selected time periods.

7. The system of claim 1, wherein the computing program, applet or application is configured to enable a medical professional to analyze patient strength data over selected time periods.

8. The system of claim 6, wherein the computing program, applet or application is configured to enable a medical professional to adjust stimulation parameters based on the analysis of the range of motion data over selected time periods.

9. The system of claim 1, wherein the computing program, applet or application is configured to enable a medical professional to adjust stimulation parameters based on analysis of at least one of program parameters, frequency data, numbers of uses of the program over a selected period of time, or cumulative treatment time.

10. The system of claim 1, wherein the computing program, applet or application is configured to enable a medical professional to adjust stimulation parameters of a second patient based on analysis of usage data from a first patient.

11. The system of claim 1, wherein the computing program, applet or application is configured to remind a patient of at least one of a time to perform a stimulation session and an appointment time.

12. The system of claim 1, further comprising a wireless link between the control electronics and a computing device.

13. The system of claim 12, wherein data carried over the wireless link is encrypted.

14. The system of claim 12, wherein the computing device is a mobile phone.

15. The system of claim 12, wherein the wireless link is a Bluetooth link.

16. The system of claim 14, wherein the mobile phone includes an application for displaying usage data.

17. The system of claim 1, wherein the computing program, applet or application is configured to enable a medical professional to adjust stimulation parameters based on the analysis of at least one of galvanic skin resistance, power dissipation, or a patient temperature.

18. The system of claim 16, further including an accelerometer configured to provide acceleration data related to use of the brace.

19. The system of claim 1, wherein the at least one program stored on a first computer readable medium is dynamic, and is configured to cause different types of EMS to be applied.

20. The system of claim 1, wherein stimulation parameters are adjusted based on the usage data.

21. The system of claim 1, wherein the usage data include frequency of use.

22. The system of claim 1, wherein the usage data include how much resistance the sensor is measuring.

23. The system of claim 1, wherein the usage data include how much current is being applied.

24. The system of claim 1, wherein the usage data include how much voltage is being applied.

25. The system of claim 1, wherein the usage data include how much power the sensor is delivering.

26. The system of claim 1, wherein the usage data include force exerted on the brace.

27. The system of claim 16, wherein the usage data include range of motion angles measured by a positional encoder.

28. The system of claim 1, wherein the usage data include at least one of programs executing or past programs executed, date, information, time, and average range of motion of a joint over a fixed period of time.

29. The system of claim 1, wherein the sensor comprises a plurality of sensors each configured to be in physical contact with different portions of skin of the patient.

30. The system of claim 1, wherein the control electronics are further configured to provide the electrical muscle stimulation via a program selected from a plurality of programs.

31. The system of claim 30, wherein the control electronics further comprise a receiver configured to receive a selection of the program.

32. The system of claim 1, wherein the control electronics and the sensor are components of a brace.

33. The system of claim 32, wherein the control electronics further comprise a communication module for receiving a program from a remote computing device for execution by the control electronics.

34. The system of claim 1, further comprising an authentication button that, when pressed, is configured to indicate that the patient acquiesces to a program being executed by the control electronics.

35. The system of claim 1, wherein the control electronics further comprises a tactile feedback provider configured to provide tactile feedback to the patient during a set time or event.

* * * * *